United States Patent
Speckmann et al.

(10) Patent No.: US 12,342,842 B2
(45) Date of Patent: Jul. 1, 2025

(54) PREPARATION FOR USE IN ENHANCING FORMATION OF SHORT-CHAIN FATTY ACIDS (SCFAS)

(71) Applicant: Evonik Operations GmbH, Essen (DE)

(72) Inventors: Bodo Speckmann, Kahl (DE); Michael Schwarm, Alzenau (DE); Ines Ochrombel, Essen (DE); Stefan Pelzer, Gütersloh (DE)

(73) Assignee: Evonik Operations GmbH, Essen (DE)

( * ) Notice: Subject to any disclaimer, the term of this patent is extended or adjusted under 35 U.S.C. 154(b) by 782 days.

(21) Appl. No.: 17/612,755

(22) PCT Filed: May 18, 2020

(86) PCT No.: PCT/EP2020/063794
§ 371 (c)(1),
(2) Date: Nov. 19, 2021

(87) PCT Pub. No.: WO2020/234230
PCT Pub. Date: Nov. 26, 2020

(65) Prior Publication Data
US 2022/0312816 A1    Oct. 6, 2022

(30) Foreign Application Priority Data

May 23, 2019 (EP) .................... 19176061

(51) Int. Cl.
*A23L 33/12* (2016.01)
*A23C 9/13* (2006.01)
*A23C 19/093* (2006.01)
*A23L 33/175* (2016.01)
*A61K 9/00* (2006.01)
*A61K 31/202* (2006.01)

(52) U.S. Cl.
CPC ............ *A23L 33/12* (2016.08); *A23C 9/1315* (2013.01); *A23C 19/093* (2013.01); *A23L 33/175* (2016.08); *A61K 9/0053* (2013.01); *A61K 31/202* (2013.01)

(58) Field of Classification Search
CPC ..... A23L 33/12; A23L 33/175; A23C 9/1315; A23C 19/093; A61K 9/0053; A61K 31/202
See application file for complete search history.

(56) References Cited

U.S. PATENT DOCUMENTS

| 5,792,795 A | 8/1998 | Buser et al. |
| 5,948,818 A | 9/1999 | Buser et al. |
| 2017/0119841 A1 | 5/2017 | Mathias et al. |

FOREIGN PATENT DOCUMENTS

| EP | 0 825 858 B1 | 5/2005 |
| WO | WO 2019/008101 A1 | 1/2019 |
| WO | WO 2019/034698 A1 | 2/2019 |

OTHER PUBLICATIONS

Li et al. (Bioscience of Microbiota, Food and Health 36(4), 135-140 (2017).*
Liu et al., lipids in healthand disease (2013), 12:109 (10pages).*
International Search Report and Written Opinion issued on Jul. 17, 2020 in PCT/EP2020/063794 filed May 18, 2020, 10 pages.

* cited by examiner

*Primary Examiner* — Shirley V Gembeh
(74) *Attorney, Agent, or Firm* — Oblon, McClelland, Maier & Neustadt, L.L.P.

(57) ABSTRACT

The invention discloses preparations for use in enhancing formation of short-chain fatty acids (SCFAs) in a subject for treating or preventing a disease or disorder comprising at least one omega-3 fatty acid salt having an organic counter ion selected from lysine, arginine, ornithine, choline and mixtures of the same, wherein the omega-3 fatty acid is selected from eicosapentaenoic acid (EPA) and docosahexaenoic acid (DHA), and a colon-specific delivery system.

17 Claims, 4 Drawing Sheets

Figure 1:
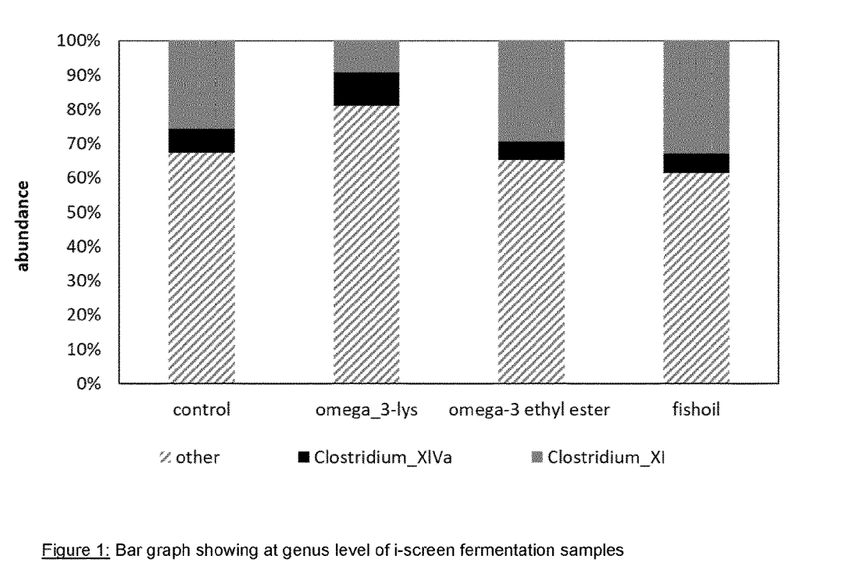

Figure 1: Bar graph showing at genus level of i-screen fermentation samples

Figure 2:
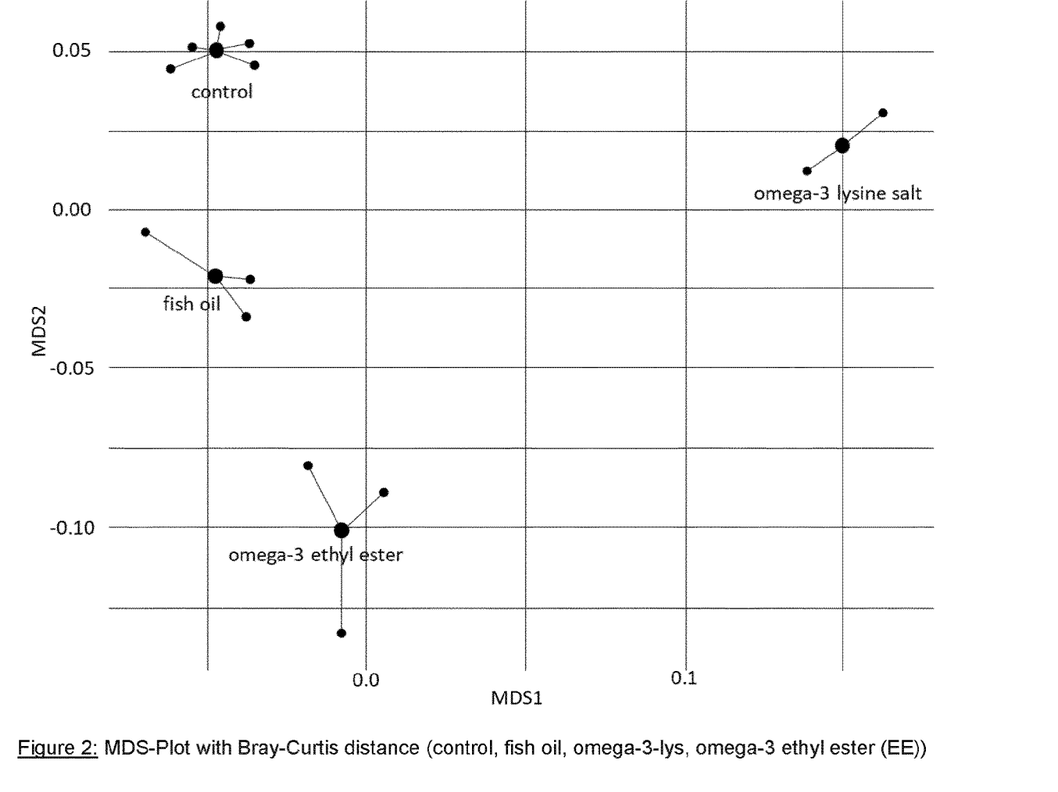

Figure 2: MDS-Plot with Bray-Curtis distance (control, fish oil, omega-3-lys, omega-3 ethyl ester (EE))

Figure 3:
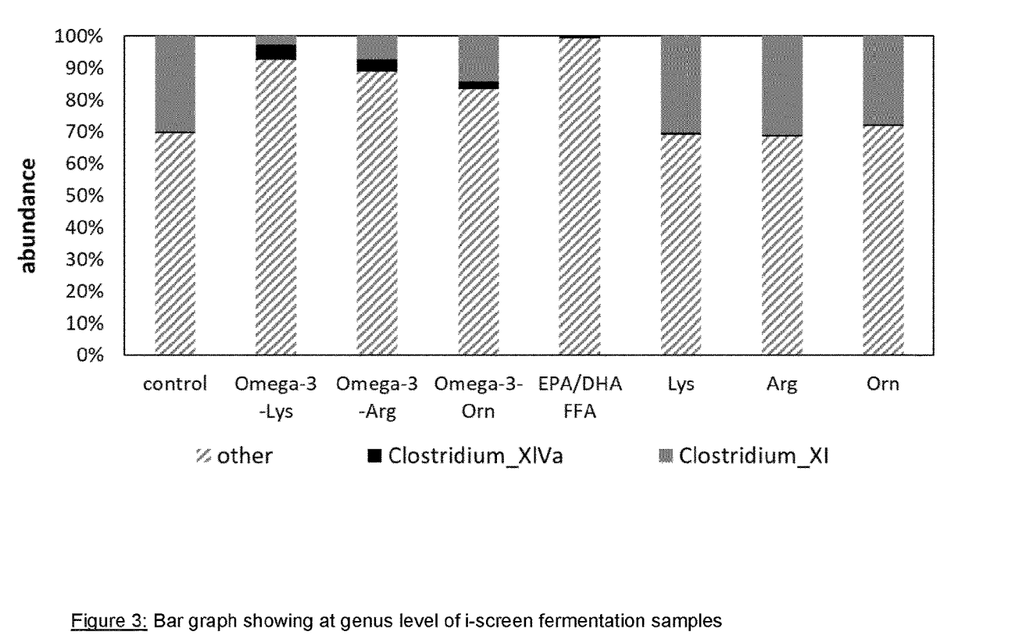

Figure 3: Bar graph showing at genus level of i-screen fermentation samples

Figure 4:
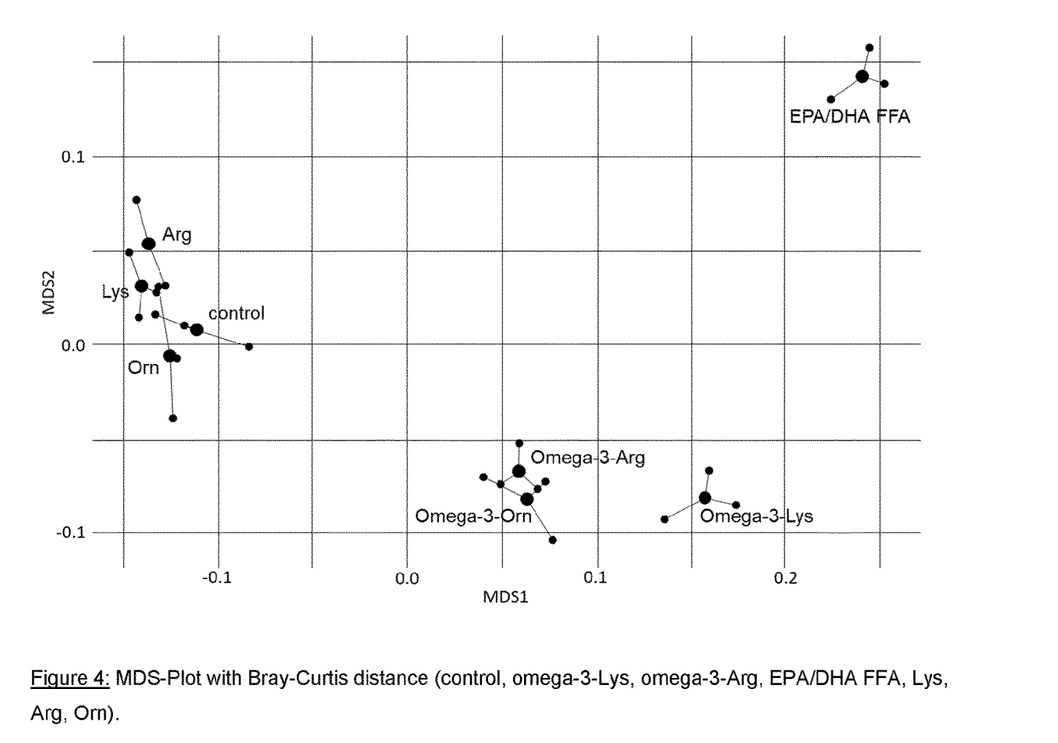

Figure 4: MDS-Plot with Bray-Curtis distance (control, omega-3-Lys, omega-3-Arg, EPA/DHA FFA, Lys, Arg, Orn).

PREPARATION FOR USE IN ENHANCING FORMATION OF SHORT-CHAIN FATTY ACIDS (SCFAS)

The current invention concerns a preparation for use in enhancing formation of the short-chain fatty acid (SCFA) propionate in a subject for treating or preventing a disease or disorder comprising at least one omega-3 fatty acid salt having an organic counter ion selected from lysine, arginine, ornithine, choline and mixtures of the same, wherein the omega-3 fatty acid is selected from eicosapentaenoic acid (EPA) and docosahexaenoic acid (DHA), and a colon-specific delivery system.

Dietary intake of omega-3 fatty acids, namely alpha-linoleic acid (ALA), EPA and DHA, is beneficial for human health, in particular with respect to e.g. the amelioration of rheumatoid arthritis and reduction of cardiovascular disease risk factors [1, 2]. Various seafoods are a source of dietary EPA/DHA, but their consumption is often not sufficient to meet the recommended dietary allowance (typically 500 mg EPA and DHA per day) [3]. This gap is closed by the widespread use of dietary supplements or fortified foods containing omega-3s [4]. Dietary supplements are concentrated sources of nutrients or other substances with a nutritional or physiological effect, whose purpose is to supplement the normal diet (www.efsa.europa.eu/en/topics/topic/food-supplements). For example, omega-3 supplements often contain either triglycerides or omega-3 ethyl esters of EPA/DHA from fish oil, krill oil, or algae.

Omega-3 fatty acids in general have anti-inflammatory, cardio- and neuroprotective effects [2, 5]. Their modes of action involve e.g. direct scavenging of reactive oxygen species, alteration of cell membrane fluidity, which subsequently affects cellular signaling events, modulation of the activity of transcription factors such as PPARG and NFKappaB that orchestrate the biosynthesis of pro- and anti-inflammatory cytokines, and competitive exclusion of substrates that are converted to proinflammatory cytokines by cyclooxygenases and lipoxygenases.

In addition to that and more recently, some animal studies have indicated that omega-3 fatty acids may also have effects on intestinal microbiota. Mice that were given diets with supplemental omega-3 of various types & sources (mainly fish oil) had increased levels of *Bifidobacterium* spp. or *Lactobacillus* spp. [6-9]. These observations are however limited to murine intestinal microbiota and to the use of standard i.e. esterified omega-3 compounds such as fish oil. A human study assessed effects of high dose fish oil intake in the form of capsules and fortified drinks on faecal microbiota composition [10]. The study showed only minor effects, unsurprisingly, because the bulk of omega-3 fatty acids will have been absorbed in the small intestine and not have reached the colon.

A study design for testing different chemical forms of omega-3 fatty acids on activity and/or composition of human intestinal microbiota has not been disclosed so far. Broadening our understanding of possible microbiota-targetable effects of omega-3s would not only be of scientific interest but may also pave the way for new prebiotic strategies to tackle conditions that are linked to dysbiosis and/or a dysfunctional microbiota, e.g. inflammatory bowel diseases, colon cancer, obesity, and type 2 diabetes. A detailed comparative analysis of the impact of different omega-3 compounds (esterified versus non-esterified) on human intestinal microbiota composition and activity is however missing.

Therefore, it was an objective of the present invention to provide new applications of omega-3 acids for promoting production of the favorable SCFA, such as propionate in the gastrointestinal tract.

This invention describes novel and surprising findings of unique and significant effects of omega-3 fatty acids in the form of free fatty acids or amino acid salts and the application of such effects in suitable formulations that can be used as e.g. nutritional supplements to achieve health effects in humans and animals through modulation of the intestinal microbiome. The omega-3 forms that are commonly used in food fortification or nutritional supplements are krill oil, fish oil, or ethyl esters derived from the former. However, formulations comprising EPA/DHA, which are used for the treatment and prevention of inflammatory diseases are mostly released in the intestine and the omega-3 fatty acids are absorbed in the small intestine. The positive effect of omega-3 fatty acids for treatment of inflammatory diseases is mostly related to uptake of fatty acids in the blood. Recently, a technology has been described to stabilize EPA/DHA free fatty acids with amino acids resulting in solid and somewhat inert salts of EPA/DHA that can be introduced into e.g. food or supplement preparations. WO2016102323A1 describes compositions comprising polyunsaturated omega-3 fatty acid salts that can be stabilized against oxidation.

A subject of the present invention is therefore a preparation for use in enhancing formation of the short-chain fatty acid (SCFA) propionate in a subject for treating or preventing a disease or disorder comprising at least one omega-3 fatty acid salt having an organic counter ion selected from lysine, arginine, ornithine, choline and mixtures of the same, wherein the omega-3 fatty acid is selected from eicosapentaenoic acid (EPA) and docosahexaenoic acid (DHA), and a colon-specific delivery system.

In particular, the present invention is directed to a preparation for use in treating or preventing a disease or disorder by enhancing formation of the short-chain fatty acid (SCFA) propionate in a subject, the disease or disorder preferably related to weight management, gut health, cardiovascular health, metabolic health, or immune health, and more preferably obesity, adipositas, type 2 diabetes, metabolic syndrome, hyperlipidemia, hypercholesterolemia, fatty liver disease, liver cirrhosis, hepatic encephalopathy, arteriosclerosis, coronary heart disease, heart failure, multiple sclerosis.

It was discovered that such amino acid salts of EPA/DHA, in particular with L-lysine, L-arginine, and L-ornithine induce favorable shifts in the SCFA profile of human colonic microbiota. This includes a reduction of branched-chain short fatty acids iso-butyrate and iso-valerate, both linked to possible adverse health effects. On the other hand, levels of even-chain fatty acids, in particular propionate, are consistently increased upon supplementation with omega-3 salts. The propionate-to-acetate ratios are likewise increased by omega-3 salts. Importantly, these effects do not arise upon supplementation with standard omega-3 compounds (fish oil, ethyl esters) nor equimolar amounts of the free fatty acid or respective amino acids alone, used as controls. Such distinction extends to the modulation of the human intestinal microbiota composition: omega-3 salts have stronger and more significant effects than fish oil, omega-3 ethyl esters, and the above-mentioned controls. In particular, *Clostridium* group XIVa, *Sutterella*, *Butyricoccus*, *Allisonella*, *Bacteroides*, *Prevotella*, and *Lactobacillus* spp. are expanded, whereas the amount of (unfavorable) bacteria of *Clostridium* group XI is decreased in the gut microbiome.

In a preferred configuration of the present invention, the preparation comprises EPA and DHA.

In a preferred configuration, the basic amino acid is selected from one or more of the following: L-lysine, L-arginine, L-ornithine.

The preparation for use according to the present invention comprises at least 10 weight-% of omega-3 fatty acid, preferably at least 20 weight-%, more preferably at least 30 weight-%, most preferably at least 40 weight-%. In a further preferred configuration, the preparation comprises at least 50 weight-% of omega-3 fatty acid, or at least 60 weight-%, or at least 70 weight-%, or at least 80 weight-%, or at least 90 weight-% of omega-3 fatty acid.

Naturally, free fatty acids are absorbed in the small intestine and are therefore not available in the large intestine. Another aspect of the invention is therefore the use of preparations containing omega-3 salts or free fatty acid in targeted-release formulations with enteric coatings. A targeted-release formulation according to the present invention is a formulation which ensures the delivery of the omega-3 fatty acids to a specific target in the body. A preferred formulation of such preparations promotes enteral or colonic delivery in the lower small intestine or in the large intestine. The targeted-release formulation can be obtained by adding enteric polymers to the matrix of the dosage form, or by adding a coating to the dosage form, preferably an enteric coating.

According to the present invention, a colon-specific delivery system is a delivery system, which targets the substance or drug directly to the colon. The advantage of a colon-specific delivery system is the local action, in case of disorders like ulcerative colitis, Crohn's disease, irritable bowel syndrome, and carcinomas. Targeted drug delivery to the colon in these cases ensures direct treatment at the site with lower dosing and fewer systemic side effects. In addition to local therapy colon can also be utilized as the portal entry of the drugs into systemic circulation for example molecules that are degraded/poorly absorbed in upper gut such as proteins and peptides may be better absorbed from the more benign environment of the colon. Colon-specific drug delivery is considered beneficial in the treatment of colon-related diseases and the oral delivery of protein and peptide drugs. Generally, each colon-specific drug delivery system has been designed based on one of the following mechanisms with varying degrees of success; 1. Coating with pH dependent polymers, 2. Coating with pH independent biodegradable polymers and 3. Delivery systems based on the metabolic activity of colonic bacteria.

By targeting the omega-3 fatty acids directly into the colon, the fatty acids can promote the formation of short-chain fatty acids locally, which then have beneficial effects in the organism.

An enteric coating is a barrier applied on oral medication that prevents its dissolution or disintegration in the gastric environment. Most enteric coatings work by presenting a surface that is stable at the intensely acidic pH found in the stomach but breaks down rapidly at a higher pH (alkaline pH). For example, they will not dissolve in the gastric acids of the stomach (pH ~3), but they will start to dissolve in the environment present in the distal small intestine (pH range proximal to distal small intestine is ~5.6 to 7.4) [11]. Colon targeted (drug) delivery systems are designed to selectively release a drug in response to the colonic environment without premature drug release in the upper GI tract.

The colon-specific delivery system can comprise a pH-dependent drug delivery system, since the colon exhibits a relatively higher pH than the upper GI tract. Accordingly, a colon-targeted delivery system is designed by using pH-dependent polymers such as cellulose acetate phthalates (CAP), hydroxypropyl methyl-cellulose phthalate (HPMCP) 50 and 55, copolymers of methacrylic acid and methyl methacrylate (e.g., Eudragit® S 100, Eudragit® L, Eudragit® FS, and Eudragit® P4135 F).

Therefore, in an advantageous configuration, the colon-specific delivery system comprises a coating comprising at least one pH dependent polymer or biodegradable polymer, preferably selected from methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, shellac, cellulose acetate trimellitate, sodium alginate, zein.

As a coating it is preferred to use a polymer polymerized from 10 to 30% by weight methyl methacrylate, 50 to 70% by weight methyl acrylate and 5 to 15% by weight methacrylic acid.

The polymer dispersion as disclosed may preferably comprise 15 to 50% by weight of a polymer polymerized from 20 to 30% by weight methyl methacrylate, 60 to 70% by weight methyl acrylate and 8 to 12% by weight methacrylic acid. Most preferred the polymer is polymerized from 25% by weight methyl methacrylate, 65% by weight methyl acrylate and 10% by weight methacrylic acid.

A 30% by weight aqueous dispersion of a polymer polymerized from 25% by weight methyl methacrylate, 65% by weight methyl acrylate and 10% by weight methacrylic acid corresponds to the commercial product EUDRAGUARD® biotic.

The percentages of the monomers add up to 100%. The functional polymer is applied in amounts of 2-30 mg/cm$^2$, preferably 5-20 mg/cm$^2$.

Another preferred configuration of the present invention are liposomal formulations of omega-3 components for use according to the present invention. Liposomal formulations preferably consist of phospholipid mixtures (e.g. deoiled sunflower lecithin) or defined phospholipids, e.g. Dioleylphospatidylcholine (DOPC).

Therefore, one further aspect of the present invention is related to a preparation for use comprising a dispersion of at least one phospholipid, and at least one omega-3 fatty acid salt, preferably omega-3 fatty acid salts having an organic counter ion selected from lysine, arginine, ornithine, choline and mixtures of the same.

A dispersion according to the present invention is according to the IUPAC definition a material comprising more than one phase where at least one of the phases consists of finely divided phase domains, often in the colloidal size range, dispersed throughout a continuous phase. The two phases may be in the same or different states of matter. They are different from solutions, where dissolved molecules do not form a separate phase from the solute. The present invention is referring both to dispersions of a liquid phase in a liquid medium as colloid (miniemulsion or microemulsion) or as suspension (emulsion with particle size over 1 µm) and to dispersions of a solid phase in a liquid medium as colloid (sol) or as suspension (with p article size over 1 µm). Moreover, the invention is also related to a dispersion of a solid phase in a solid continuous medium, which is referred to as a solid sol.

In an alternative configuration of the present invention the phospholipid is a deoiled phospholipid comprising a phosphatidylcholine content of greater than 40 weight-%, preferably 70 weight-%, preferably greater 90 weight-% and a phosphatidylethanolamine content of lower than 5 weight-%, preferably lower than 1 weight-%.

In an alternative embodiment the phospholipid is a non-hydrogenated phospholipid having an oleic and/or linoleic acid content of greater than 70 weight-% of total fatty acids.

In a further preferred configuration of the present invention the mass ratio of phospholipid to fatty acid salt is greater than 0.005, preferably greater than 0.01, more preferably greater than 0.09, most preferably greater than 0.39.

In an alternative embodiment the preparation is in the form of a powder or of a liquid that result in colloidal dispersions with mean particle sizes of smaller than 1 µm, preferably smaller than 500 nm, most preferably smaller than 250 nm when mixed with water at a pH value between pH 6.5 and 7.5.

In another embodiment the components are finely dispersed in each other so that both phospholipid and fatty acid salts are present and detectable in amounts of 100 µg and smaller.

One subject of the present invention is the use of a preparation according to the present invention as a feed or food supplement or its use in foodstuffs. Preferred foodstuffs according to the invention are dairy products, in particular yoghurt, cheese, milk, fermented milk, butter, quark, and sour cream. Further foodstuffs according to the invention are meal replacement compositions and formula diets for weight management, mueslis, muesli bars, snack bars, bread, chocolates, and gummies.

A further subject of the present invention is a feed- or foodstuff composition containing a preparation according to the present invention and at least one further feed or food ingredient, preferably selected from proteins, carbohydrates, fats, further prebiotics, preferably pectins, enzymes, vitamins, immune modulators, milk replacers, minerals, amino acids, preferably L-ornithine L-aspartate, L-ornithine, L-asparagine, coccidiostats, acid-based products, medicines, and combinations thereof.

The feed- or foodstuff composition according to the present invention does also include dietary supplements in the form of a pill, capsule, tablet or liquid.

A further subject of the current invention is a pharmaceutical composition containing a preparation according to the present invention and a pharmaceutically acceptable carrier.

An advantageous configuration according to the present invention is a composition for improving the health status of an animal or a human being by one or more of the following:
- increasing the total amount of bacteria of *Clostridium* group XIVa, *Sutterella, Butyricoccus, Allisonella, Bacteroides, Prevotella, Lactobacillus* in the gut microbiome,
- reducing the total amount of bacteria of *Clostridium* group XI in the gut microbiome,
- increasing production of short chain fatty acids, preferably propionate, and
- inhibiting formation of branched-chain short-chain fatty acids, preferably iso-butyrate and iso-valerate.

WORKING EXAMPLES

Intestinal Screening Model

To determine the effect of omega-3 compounds on adult colonic microbiota, an intestinal screening model was used (I-screen, TNO, the Netherlands), which corresponds to colonic environment. A translation of such in vitro experiment towards an application in a living organism (animal or human) requires the use of a colon-specific delivery form to circumvent absorption of fatty acids in upper parts of the gastrointestinal tract. The use of compositions comprising omega-3 compounds in formulations enabling a colon-specific delivery is part of the present invention.

The I-screen model was inoculated with standard human adult fecal microbiota material, which consisted of pooled fecal donations from six healthy adult volunteers (Caucasian, European lifestyle and nutrition). The fecal material was mixed and grown in a fed-batch fermenter for 40 hours to create a standardized microbiota as described previously [12]. These standard adult gut microbiota sets were stored at −80° C. in 12% glycerol.

The intestinal microbiota was cultured in vitro in modified standard ileal efflux medium (SIEM), the composition of which was described by Minekus et al. [13]. All components were supplied by Trititium Microbiology (Veldhoven, The Netherlands). The pH of the medium was adjusted to 5.8.

For the I-screen fermentations, the pre-cultured standardized fecal inoculum was diluted 50 times in modified SIEM. Omega-3-lysine (omega-3-lys), omega-3 ethyl ester (EE) and fish oil were introduced into the I-screen to final concentrations of 1.4 mg/ml each. The I-screen incubation was performed under following gas conditions: 0% $O_2$, 10% $CO_2$, 10% $H_2$, 80% $N_2$. All experiments were carried out in triplicates.

DNA Isolation

DNA extraction for the sequencing of 16S rRNA coding genes was performed as described by Ladirat et al. (2013) with some minor modifications. Approximately 100 µl of the culture materials were added to the wells of a 96 well plate containing per well 300 µl of lysis buffer (Mag Mini DNA Isolation Kit, LGC ltd, UK), 500 µl zirconium beads (0.1 mm; BioSpec products, Bartlesville, OK, USA) and 500 µl of phenol saturated with Tris-HCl (pH 8.0; Carl Roth GMBH, Germany). The 96 well plate was placed in a Mini-BeadBeater-96 (BioSpec products, Bartlesville, OK, USA) for 2 min at 2100 oscillations/min. DNA was subsequently purified using the Agowa Mag Mini DNA Isolation Kit according to the manufacturer recommendations. Extracted DNA was eluted in a final volume of 60 µl buffer.

V4 16S rRNA Gene Sequencing

The microbiota composition was analyzed by 16S rRNA gene amplicon sequencing of the V4 hypervariable region. This was achieved through a series of steps:

The amount of bacterial DNA in the i-screen DNA samples was determined by quantitative polymerase chain reaction (qPCR) using primers specific for the bacterial 16S rRNA gene: Forward primer: CGAAAGCGTGGG-GAGCAAA; Reverse primer: GTTCGTACTCCCCAGGCGG; Probe: 6FAM-ATTAGA-TACCCTGGTAGTCCA-MGB.

Subsequently, PCR amplicons of the V4 hypervariable region of the 16S rRNA gene were generated for the individual samples by amplification of 500 pg of DNA as described by Kozich et al. (2013), using F515/R806 primers (Caporaso et al. 2011). Primers included Illumina adapters and a unique 8-nt sample index sequence key (Kozich et al. 2013). A mock control was included for technical quality control. The amount of amplified DNA per sample was quantified using the dsDNA 910 Reagent Kit on the Fragment Analyzer (Advanced Analytical). The amplicon libraries were pooled in equimolar amounts and purified from 1.2% agarose gel using the Gel Extraction Kit (Qiagen). The Library was quantified using the Quant-iT™ PicoGreen® dsDNA Assay Kit (Thermo Fisher Scientific). Paired-end sequencing of amplicons was conducted on the Illumina MiSeq platform (Illumina, Eindhoven, The Netherlands).

The sequence data was processed with Mothur v.1.36.1 (Schloss et al., 2009) in line with the mothur MiSeq SOP (Kozich et al., 2013). Before merging the read pairs, low quality regions were trimmed using Btrim (Kong, 2011) with a sliding window size of 5 nt and average quality score of 25. After merging, the sequences were filtered by length while no ambiguous bases were allowed. The unique sequences were aligned to the bacterial SILVA SEED reference alignment release 102 (available at: http://www.mothur.org/wiki/Silva_reference_files); too short sequences were removed using screen.seqs with parameters "optimize=start-end, criteria=90". Chimeric sequences were identified per sample using UCHIME (Edgar et al., 2011) in de novo mode and removed. Next, sequences occurring less than 10 times in the entire dataset were removed. Taxonomic names were assigned to all sequences using the Ribosomal Database Project (RDP) naïve Bayesian classifier with confidence threshold of 60% and 1000 iterations (Wang et al., 2007) and the mothur-formatted version of the RDP training set v.9 (trainset9_032012).

Sequences were grouped using Minimum Entropy Decomposition (MED) algorithm that clusters 16S rRNA gene amplicons in a sensitive manner (Eren et al., 2105). To filter noise, the "minimum substantive abundance" filter was set to 200.

Polyunsaturated Fatty Acid Compositions

In the examples for the present invention, different polyunsaturated fatty acid compositions were used. Different omega-3 fatty acid salts having an organic counter ion selected from the basic amino acids lysine, arginine and ornithine were prepared. The omega-3 fatty acids Eicosapentaenoic acid (C20:5w3c) (EPA) and Docosahexaenoic acid (C22:6w3c) (DHA) are present in a ratio of around 2:1 (ratio EPA:DHA).

The omega-3 lysine salt (omega-3-lys) contains around 32 weight-% of L-lysine and around 65 weight-% of polyunsaturated fatty acids. The major polyunsaturated fatty acids in the composition are the omega-3 fatty acids Eicosapentaenoic acid (C20:5w3c) (EPA) and Docosahexaenoic acid (C22:6w3c) (DHA), summing up to around 58 weight-% of the composition. The composition also contains minor amounts of Docosaenoic acid isomer (incl. erucic acid) (C22:1), Docosapentaenoic acid (C22:5w3c) and of the omega-6 fatty acids Arachidonic acid (C20:4w6) and Docosatetraenoic acid (C22:4w6c).

The omega-3 arginine salt (omega-3-arg) contains around 35 weight-% of L-arginine and around 64 weight-% of polyunsaturated fatty acids. The major polyunsaturated fatty acids in the composition are the omega-3 fatty acids Eicosapentaenoic acid (C20:5w3c) (EPA) and Docosahexaenoic acid (C22:6w3c) (DHA), summing up to around 49 weight-% of the composition. The composition also contains minor amounts of Docosaenoic acid isomer (incl. erucic acid) (C22:1), Docosapentaenoic acid (C22:5w3c) and of the omega-6 fatty acids Arachidonic acid (C20:4w6) and Docosatetraenoic acid (C22:4w6c).

The omega-3 ornithine salt (omega-3-orn) contains around 29 weight-% of L-ornithine and around 70 weight-% of polyunsaturated fatty acids. The major polyunsaturated fatty acids in the composition are the omega-3 fatty acids Eicosapentaenoic acid (C20:5w3c) (EPA) and Docosahexaenoic acid (C22:6w3c) (DHA), summing up to around 54 weight-% of the composition. The composition also contains minor amounts of Docosaenoic acid isomer (incl. erucic acid) (C22:1), Docosapentaenoic acid (C22:5w3c) and of the omega-6 fatty acids Arachidonic acid (C20:4w6) and Docosatetraenoic acid (C22:4w6c).

Example 1: Omega-3-Lysine Salt has Unique Effects on the Composition of a Human Colonic Microbiota The presence of omega-3-lys influences the microbial community by a shift to a decreased *Clostridium* group XI (from 26% to 9%) and an increased *Clostridium* group XIVa (from 7% to 10%) compared to the control (FIG. 1), which is linked to strong beneficial effects on gut health. The addition of fish oil or omega ethyl ester (EE) had no positive effect on the microbial community. Furthermore, the significance of these effects is confirmed by a statistical MDS-plot, which shows the Bray-Curtis distance (FIG. 2).

Omega-3-lys has a strong and significant impact on microbiota variance, which exceeds the effects of esterified omega-3 compounds and also that of the standard prebiotic inulin (table 1). Omega-3-lys, omega-3 ethyl ester, and fish oil were applied at final concentrations of 1.4 mg/ml, inulin at 4 mg/ml. Values are given as means of triplicate experiments.

FIG. 1 shows bar graph showing at genus level of i-screen fermentation samples based on MiSeq sequencing of the V4 hypervariable region of the 16S rRNA encoding region gene. After 24 h incubation in SIEM in the presence of colon microbiota without any addition (control), addition of omega-3 lysine salt, omega-3 ethyl ester and fish oil, respectively.

FIG. 2 shows an MDS-Plot with Bray-Curtis distance (control, fish oil, omega-3-lys, omega-3 ethyl ester (EE)).

TABLE 1

Effects of omega-3-lys, EE, fish oil, and inulin versus control on the colonic microbiota after 24 h incubation. Both explained variance and p-value are given. Variance explained is the proportion of variance within the microbiota that can be explained by the effect of the substance compared to the control.

| Omega-3 compound | Effect on colonic microbiota after 24 h incubation | p-value |
|---|---|---|
| Omega-3-lys | 61.5% | 0.012 |
| EE | 44.5% | 0.013 |
| Fish oil | 26.1% | 0.017 |
| Inulin | 40.2% | 0.01 |

Example 2: Omega-3-Lys Salt Reduces the Iso-Butyrate and Iso-Valerate Formation in a Human Colonic Microbiota To test effects of the different omega-3-compounds on the production of short-chain fatty acids (SCFA) by human microbiota the substances were applied at final concentrations of 1.4 mg/ml and incubated for 24 h as described in example 1.

For the analysis of SCFA in exposed material from the I-screen samples were centrifuged (~4000 g, 5 min), clear supernatant was filter sterilized (0.45 μm) and a mixture of formic acid (20%), methanol and 2-ethyl butyric acid (internal standard, 2 mg/ml in methanol) was added. A 3 μl sample with a split ratio of 75.0 was injected on a GC-column (ZB-5HT inferno, ID 0.52 mm, film thickness 0.10 μm; Zebron; Phenomenex, USA) in a Shimadzu GC-2014 gas chromatograph. SCFA parameters analyzed were: acetic acid, propionic acid, n-butyric acid, iso-butyric acid, and iso-valerate.

Omega-3-lys decreases, whereas omega-3 ethyl ester and fish oil increase levels of SCFA iso-butyrate and iso-valerate compared to the control in a human intestinal microbiota (table 2). The reduction of iso-forms of butyrate and valerate indicates decreased protein fermentation in the gut, and a reduction of harmful fermentation products.

TABLE 2

After 24 h incubation in SIEM with human colon microbiota measured changes of iso-butyrate, and iso-valerate concentrations in mM compared to the control in the presence of omega-3-lys, ethyl ester (EE), or fish oil, respectively.

| Omega-3 compound | Iso-butyrate [mM] (change in mM) | Iso-valerate [mM] (change in mM) |
| --- | --- | --- |
| Control | 1.36 (0) | 3.56 (0) |
| Omega-3-lys | 0.63 (−0.73) | 1.92 (−1.64) |
| EE | 1.70 (+0.34) | 4.03 (+0.47) |
| Fish oil | 1.91 (+0.55) | 4.15 (+0.59) |

Example 3: Omega-3-Lys Salt Increases Propionate Formation and Propionate-to-Acetate Ratio in a Human Colonic Microbiota The addition of omega-3-lys accelerate propionate production by human microbiota (table 3). Incubations and SCFA analyses were performed as described for examples 1 and 2.

In the presence of omega-3-lys the amount was 1.38 mM higher than in the control. By this increased propionate formation, the propionate-to-acetate ratio is also increased. The addition of fish oil and EE has no significant effects on the propionate production of the microbiota and its propionate/acetate ratio. Propionate is beneficial for the health status of the human gut, because it can be incorporated into gluconeogenesis.

TABLE 3

Omega-3-lys affects even-chain SCFA levels in a human colonic microbiota differently than omega-3 ethyl ester and fish oil. All compounds were applied at final concentrations of 1.4 mg/ml. Values are given as means of triplicate experiments.

| Omega-3 compound | Acetate [mM] (change in mM) | Propionate [mM] (change in mM) | propionate/acetate ratio |
| --- | --- | --- | --- |
| Control | 38.76 (0) | 8.73 (0) | 0.23 |
| Omega-3-lys | 35.55 (−3.21) | 10.11 (+1.38) | 0.28 |
| EE | 35.84 (−2.92) | 8.71 (−0.02) | 0.24 |
| Fish oil | 36.46 (−2.30) | 8.55 (−0.17) | 0.23 |

Example 4: Omega-3-Lys, -Arg, and -Orn Salts have Unique Effects on the Composition of a Human Colonic Microbiota, which are not Mimicked by the EPA/DHA FFA or Respective Amino Acids Alone To test effects of different omega-3-compounds (1.4 mg/ml each), EPA/DHA free fatty acids (FFA) (0.95 mg/ml) and respective amino acids (0.5 mg/ml each) on the microbial composition of human colon material, incubations were performed as described for Example 1, except that microaerophilic conditions were applied: The 1-screen incubation was performed under following gas conditions: 0.2% $O_2$, 0.2% $CO_2$, 10% Hz, 89.6% Nz. The addition of Omega-3-lys, -arg, and -orn salts have a significant positive effect of the Clostridium XIVa group, which cannot be observed by the addition of FFA or the respective amino acids alone (FIG. 3). The abundance of the Clostridium XIVa group increases from 0.6% up to at least 2% of the total community. Furthermore, the Clostridium group XI is decreased from 30% abundance of the total community by the addition of omega-3-lys, -arg, and -orn salts to values below 15%. The increase of Clostridium XIVa group and the decrease of Clostridium XI group is beneficial for the health status of the human colon microbiota. Furthermore, the significance of these effects is confirmed by the statistical analyses (FIG. 4).

FIG. 3 shows bar graph showing at genus level of i-screen fermentation samples based on MiSeq sequencing of the V4 hypervariable region of the 16S rRNA encoding region gene. After 24 h incubation in SIEM in the presence of colon microbiota without any addition (control), addition of omega-3 lysine salt (omega-3-Lys), omega-3 arginine salt (omega-3-Arg), EPA/DHA free fatty acids (EPA/DHA FFA), lysine (Lys), arginine (Arg), or ornithine (Orn), respectively.

FIG. 4 shows an MDS-Plot with Bray-Curtis distance (control, omega-3-Lys, omega-3-Arg, EPA/DHA FFA, Lys, Arg, Orn).

Example 5: Omega-3-Lys, -Arg, and -Orn Salts Reduce the Iso-Butyrate and Iso-Valerate Formation in a Human Colonic Microbiota, which are not Mimicked by the Respective Amino Acids Alone The addition of omega-3 amino acid salts (1.4 mg/ml each), and EPA/DHA FFA (0.95 mg/ml) have negative influence on the level of iso-valerate production when added to the human microbiota. Incubations and SCFA analyses were performed as described for examples 1 and 2.

The concentration is significantly decreased in the i-screen compared to the single amino acids (0.5 mg/ml), respectively (table 4). Omega-3 amino acid salts decrease, whereas the respective amino acids increase branched-chain SCFA levels in a human intestinal microbiota. This can be an indication of lowered protein fermentation process in the gut, which also indicates a reduced production of harmful by-products.

TABLE 4

After 24 h incubation in SIEM measured iso-butyrate, and iso-valerate concentrations in mM in the presence of different omega-3 amino acid salts, EPA/DHA FFA, L-lysine, L-arginine, and L-ornithine, respectively. Values are given as means of triplicate experiments.

| Omega-3 compound | Iso-butyrate [mM] | Iso-valerate [mM] |
| --- | --- | --- |
| Control | 1.21 | 2.74 |
| Omega-3-lys | 0.33 | 1.15 |
| Omega-3-arg | 0.45 | 1.49 |
| Omega-3-orn | 0.80 | 2.43 |
| FFA | 0 | 0.25 |
| Lys | 1.47 | 3.57 |
| Arg | 1.21 | 3.71 |
| Orn | 1.37 | 3.31 |

Example 6: Omega-3-Lys, and -Arg Salts Increase Propionate Formation and Propionate-to-Acetate Ratio in a Human Colonic Microbiota Incubations and SCFA analyses were performed as described for examples 1, 2, and 3. The addition of the omega-3-lys, -arg, and -orn salts increased propionate formation compared to the controls in a human intestinal microbiota (table 5). Furthermore, the addition of omega-3-lys, or -arg, increases the propionate-to-acetate ratio. Omega-3 FFA had a minor effect on propionate levels but strongly reduced acetate levels, resulting in an increased propionate-to-acetate ratio compared to control.

Propionate is beneficial for the health status of the human gut, because it can be incorporated into gluconeogenesis.

TABLE 5

Effects of omega-3 amino acid salts and controls on even-chain SCFA levels in a human colonic microbiota.

| Compound | Propionate [mM] | Acetate [mM] | Propionate/acetate ratio |
|---|---|---|---|
| Control | 7.37 | 15.21 | 0.48 |
| Omega-3-lys | 9.65 | 13.96 | 0.69 |
| Omega-3-arg | 9.59 | 14.90 | 0.64 |
| Omega-3-orn | 8.91 | 19.98 | 0.45 |
| Lys | 9.49 | 24.03 | 0.40 |
| Arg | 9.39 | 23.50 | 0.40 |
| Orn | 9.11 | 25.36 | 0.36 |
| Omega-3 FFA | 7.52 | 9.02 | 0.83 |

Compounds were applied at the following concentrations: Omega-3 amino acid salts = 1.4 mg/ml; EPA/DHA FFA = 0.96 mg/ml; L-lysine = 0.49 mg/ml; L-arginine = 0.52 mg/ml; L-ornithine = 0.5 mg/ml. Values are given as means of triplicate experiments Example 7: Capsules Comprising Omega-3 Amino Acid Salts HPMC capsules (size 3) were filled with omega-3 amino acid salts: omega-3-lys, omega-3-arg and omega-3-orn. The total capsule weight was 200 mg. The capsules were coated with an enteric coating composition as shown in table 6.

TABLE 6

Coating composition

| Compound | Dry substance [g] | Content based on coating [%] | Weight gain [%] | Content based on capsule [%] |
|---|---|---|---|---|
| EUDRAGUARD ® biotic | 40.8 | 36.9 | 8.2 | 6.7 |
| HPMC | 43.1 | 39.0 | 8.6 | 7.1 |
| Talc | 20.4 | 18.4 | 4.0 | 3.3 |
| Polyethylene glycol | 4.3 | 3.9 | 0.9 | 0.7 |
| Triethyl citrate | 2.0 | 1.8 | 0.4 | 0.3 |

REFERENCES

1. Balk E M, Lichtenstein A H: Omega-3 Fatty Acids and Cardiovascular Disease: Summary of the 2016 Agency of Healthcare Research and Quality Evidence Review. *Nutrients* 2017, 9(8).
2. Calder P C: Marine omega-3 fatty acids and inflammatory processes: Effects, mechanisms and clinical relevance. *Biochim Biophys Acta* 2015, 1851(4):469-484.
3. Papanikolaou Y, Brooks J, Reider C, Fulgoni V L, 3rd: U.S. adults are not meeting recommended levels for fish and omega-3 fatty acid intake: results of an analysis using observational data from NHANES 2003-2008. *Nutr J* 2014, 13:31.
4. Clarke T C, Black L I, Stussman B J, Barnes P M, Nahin R L: Trends in the use of complementary health approaches among adults: United States, 2002-2012. *Natl Health Stat Report* 2015(79):1-16.
5. Schunck W H, Konkel A, Fischer R, Weylandt K H: Therapeutic potential of omega-3 fatty acid-derived epoxyeicosanoids in cardiovascular and inflammatory diseases. *Pharmacol Ther* 2018, 183:177-204.
6. Patterson E, R M O D, Murphy E F, Wall R, O O S, Nilaweera K, Fitzgerald G F, Cotter P D, Ross R P, Stanton C: Impact of dietary fatty acids on metabolic activity and host intestinal microbiota composition in C57B L/6J mice. *Br J Nutr* 2014, 111(11):1905-1917.
7. Robertson R C, Seira Oriach C, Murphy K, Moloney G M, Cryan J F, Dinan T G, Paul Ross R, Stanton C: Omega-3 polyunsaturated fatty acids critically regulate behaviour and gut microbiota development in adolescence and adulthood. *Brain Behav Immun* 2017, 59:21-37.
8. Mujico J R, Baccan G C, Gheorghe A, Diaz L E, Marcos A: Changes in gut microbiota due to supplemented fatty acids in diet-induced obese mice. *Br J Nutr* 2013, 110 (4):711-720.
9. Pachikian B D, Essaghir A, Demoulin J B, Catry E, Neyrinck A M, Dewulf E M, Sohet F M, Portois L, Clerbaux L A, Carpentier Y A et al: Prebiotic approach alleviates hepatic steatosis: implication of fatty acid oxidative and cholesterol synthesis pathways. *Mol Nutr Food Res* 2013, 57(2):347-359.
10. Watson H, Mitra S, Croden F C, Taylor M, Wood H M, Perry S L, Spencer J A, Quirke P, Toogood G J, Lawton C L et al: A randomised trial of the effect of omega-3 polyunsaturated fatty acid supplements on the human intestinal microbiota. *Gut* 2018, 67(11):1974-1983.
11. Abuhelwa A Y, Foster D J, Upton R N: A Quantitative Review and Meta-Models of the Variability and Factors Affecting Oral Drug Absorption-Part I: Gastrointestinal pH. *AAPS J* 2016, 18(5):1309-1321.
12. Ladirat S E, Schols H A, Nauta A, Schoterman M H, Keijser B J, Montijn R C, Gruppen H, Schuren F H: High-throughput analysis of the impact of antibiotics on the human intestinal microbiota composition. *J Microbiol Methods* 2013, 92(3):387-397.
13. Minekus M, Smeets-Peeters M, Bernalier A, Marol-Bonnin S, Havenaar R, Marteau P, Alric M, Fonty G, Huis in't Veld J H: A computer-controlled system to simulate conditions of the large intestine with peristaltic mixing, water absorption and absorption of fermentation products. *Appl Microbiol Biotechnol* 1999, 53(1):108-114.

The invention claimed is:

1. A colonic preparation, comprising:
   an omega-3 fatty acid salt having an organic counter ion selected from the group consisting of lysine, arginine, ornithine, choline, and a combination thereof; and
   a colon-specific delivery system selected from the group consisting of a delivery system comprising a coating with a pH dependent polymer, a delivery system comprising a coating with a pH independent biodegradable polymer, and a delivery system based on a metabolic activity of a colonic bacteria,
   wherein the omega-3 fatty acid is selected from the group consisting of eicosapentaenoic acid (EPA) and docosahexaenoic acid (DHA), and
   wherein the preparation is a powder having a mean particle size of 1 µm or less.

2. The preparation of claim 1, wherein the preparation is suitable for enhancing formation of short-chain fatty acid (SCFA) propionate in a subject for treating a disease or disorder related to weight management, gut health, cardiovascular health, metabolic health, or immune health.

3. The preparation of claim 2, wherein the disease or disorder is selected from the group consisting of obesity, adipositas, type 2 diabetes, metabolic syndrome, glucose intolerance, hyperglycemia, prediabetes, hyperlipidemia, hypercholesterolemia, fatty liver disease, liver cirrhosis, hepatic encephalopathy, arteriosclerosis, coronary heart disease, heart failure, and auto immune diseases multiple sclerosis, type 1 diabetes, psoriasis, rheumatoid arthritis, asthma bronchiale, ulcerative colitis, and Crohn's disease.

4. The preparation of claim 1, wherein the organic counter ion is at least one selected from the group consisting of L-lysine, L-arginine and L-ornithine.

5. The preparation of claim 1, wherein the colon-specific delivery system is the delivery system comprising a coating with a pH dependent polymer.

6. The preparation of claim 5, wherein the coating comprises a polymer polymerized from 10 to 30% by weight methyl methacrylate, 50 to 70% by weight methyl acrylate and 5 to 15% by weight methacrylic acid.

7. The preparation of claim 6, wherein a mass ratio of the phospholipid to the omega-3 fatty acid salt is greater than 0.005.

8. The preparation of claim 5, wherein the coating is present in an amount of from 2 to 30 mg/cm$^2$.

9. The preparation of claim 1, comprising at least 10 weight % of the omega-3 fatty acid salt.

10. The preparation of claim 1, further comprising:
a dispersion of a phospholipid and the omega-3 fatty acid salt,
wherein the phospholipid is a deoiled phospholipid comprising greater than 40 weight % of a phosphatidylcholine and lower than 5 weight % of a phosphatidylethanolamine.

11. A targeted-release formulation, comprising:
the preparation of claim 1; and
a coating.

12. The preparation of claim 1, wherein the preparation is suitable as a feed or food supplement or as a pharmaceutical product.

13. The preparation of claim 12, further comprising:
a feed or food ingredient.

14. The preparation of claim 1, wherein the preparation is suitable for improving the health status of an animal or a human being by at least one of the following:
increasing the total amount of bacteria of *Clostridium* group XIVa, *Sutterella, Butyricoccus, Allisonella, Bacteroides, Prevotella, Lactobacillus* in the gut microbiome,
reducing the total amount of bacteria of *Clostridium* group XI in the gut microbiome,
increasing production of short chain fatty acids, and
inhibiting formation of branched-chain short-chain fatty acids, preferably iso-butyrate and iso-valerate.

15. The preparation of claim 1, wherein the colon-specific delivery system is the delivery system comprising a coating with a pH independent biodegradable polymer.

16. The preparation of claim 15, wherein the coating is present in an amount of from 2 to 30 mg/cm$^2$.

17. The preparation of claim 6, wherein the preparation is a colloidal dispersion having a mean particle size of 1 μm or less.

* * * * *